United States Patent [19]

Müller et al.

[11] Patent Number: 5,270,350

[45] Date of Patent: Dec. 14, 1993

[54] CROSSLINKED SHAPED DENTAL ARTICLES

[75] Inventors: Michael Müller, Bergisch-Gladbach; Wolfgang Podszun, Cologne; Günther Bebermeier; Roland Richter, both of Leverkusen, all of Fed. Rep. of Germany

[73] Assignee: Bayer Aktiengesellschaft, Leverkusen, Fed. Rep. of Germany

[21] Appl. No.: 824,846

[22] Filed: Jan. 23, 1992

[30] Foreign Application Priority Data

Jan. 30, 1991 [DE] Fed. Rep. of Germany ....... 4102627

[51] Int. Cl.$^5$ .................................................. A61K 6/08
[52] U.S. Cl. ................................... 523/115; 523/113; 523/114
[58] Field of Search ........................ 523/113, 114, 115; 522/121, 142

[56] References Cited

U.S. PATENT DOCUMENTS

| | | | |
|---|---|---|---|
| 4,230,790 | 10/1980 | Hill | 522/121 |
| 4,337,130 | 6/1982 | Abramjian | 522/142 |
| 4,379,039 | 4/1983 | Fujimoto et al. | 522/142 |
| 4,379,695 | 4/1983 | Orlowski et al. | 523/115 |
| 4,396,476 | 8/1983 | Roemer et al. | 523/115 |
| 4,400,159 | 8/1983 | Orlowski et al. | 523/115 |
| 4,406,625 | 9/1983 | Orlowski et al. | 523/115 |
| 4,431,421 | 2/1984 | Kawahara et al. | 523/115 |
| 4,491,453 | 1/1985 | Koblitz | 523/115 |
| 4,639,500 | 1/1987 | Kubo | 522/121 |
| 4,692,396 | 9/1987 | Uchida | 522/121 |
| 4,904,737 | 2/1990 | Sato et al. | 522/121 |
| 4,952,241 | 8/1990 | Reiners et al. | 523/115 |
| 4,952,614 | 8/1990 | Reiners et al. | 523/113 |
| 4,985,343 | 1/1991 | Kushi et al. | 522/121 |
| 5,089,291 | 2/1992 | Hayama et al. | 522/121 |

OTHER PUBLICATIONS

Polymer Handbook-3rd, edition, VII/519-524, 544-557 Brandrup & Immergut (1989).

*Primary Examiner*—Veronica P. Hoke
*Attorney, Agent, or Firm*—Sprung Horn Kramer & Woods

[57] ABSTRACT

The invention relates to a process for the production of crosslinked dental mouldings, in particular for teeth made of plastic, the compositions used therefore and the articles obtained.

3 Claims, No Drawings

CROSSLINKED SHAPED DENTAL ARTICLES

The invention relates to a process for the production of crosslinked dental mouldings, in particular for teeth made of plastic, the compositions used therefore and the articles obtained.

Teeth of non-crosslinked plastic can be produced from, for example, polymethyl methacrylate by thermoplastic shaping. However, the teeth obtained do not achieve the required use properties to their full extent, so that their wear resistance and crazing resistance are inadequate.

Customary teeth made of plastic are produced by polymerisation of mixtures of

| | |
|---|---|
| 35–50% by weight | of monomer liquid containing 80–95% by weight of methyl methacrylate and 5–20% by weight of ethylene glycol dimethacrylate as the crosslinking agent |
| and | |
| 50–65% by wight | of powder of non-crosslinked polymethyl methacrylate in the form of bead polymers having an average particle size of 30–120 μm. |

Dental materials for the production of teeth made of plastic which contain (as well as non-crosslinked) crosslinked polymethyl methacrylate as the powder are proposed in U.S. No. 4,396,377. The conventional mixture of methyl methacrylate and a crosslinking agent such as ethylene glycol dimethacrylate is used as the monomer liquid. Dental materials according to U.S. No. 4,396,377 have the following composition:

| | |
|---|---|
| 0–50% | of non-crosslinked polymer |
| 10–70% | of crosslinked polymer |
| 20–66% | of monomer (which does not act as a crosslinking agent) |
| 7–27% | of crosslinking agent |

EP-A 59,525 describes materials similar to those in the abovementioned patent specification. The materials claimed have the following composition:

| | |
|---|---|
| 0–50% | of non-crosslinked polymer |
| 10–70% | of crosslinked polymer |
| 2–30% | of monomer (which does not act as a crosslinking agent) |
| 20–70% | of crosslinking agent |

Dental materials for the production of false teeth in which exclusively or predominantly crosslinking agents are used as the monomer liquid and exclusively crosslinked polymer having particular swelling properties is used as the polymer component have been disclosed in DE-A 3,820,497 and EP-A 110,092. These dental materials have the following composition:

| | |
|---|---|
| 5–35% | of crosslinked polymer |
| 0–40% | of monomer (which does not act as a crosslinking agent) |
| 40–90% | of crosslinking agent. |

DE-A 2,403,211 describes dental compositions containing filler which are characterised in that they contain exclusively microfine silicon dioxide as the filler and bisGMA or specific urethane methacrylates obtained by reaction of diisocyanates with hydroxyalkyl methacrylates as the monomer.

Teeth made of crosslinked plastic are produced by the socalled chemoplastic process. In this process, mixtures of pulverulent polymer, monomer and crosslinking agent are polymerised in metal moulds under pressure at elevated temperature. The tooth can be built up in several layers according to the natural model. A three-layered build-up with an enamel, dentine and neck layer in which the individual layers differ by the pigmentation and the crosslinking agent content is often chosen. Although teeth which are obtained by the chemoplastic process are significantly superior to those produced by thermoplastic processes in respect of wear resistance, they still do not achieve the level required for posterior teeth (see Ullmann's encyclopedia of industrial chemistry, Volume A8 Page 280, Weinheim, N.Y. 1987).

The mixture of polymer powder, monomer and crosslinking agent used in the chemoplastic process is inhomogeneous, since the polymer particles, which are usually spherical and have an average particle size of 40 to 100 μm, are not completely dissolved. The cured dental moulding is consequently also not completely homogeneous, but contains regions of non-crosslinked polymethyl methacrylate. These non-crosslinked regions are partly responsible for the inadequate wear resistance and solvent resistance.

The chemoplastic process moreover has other disadvantages: the times needed for filling, heating, polymerising, cooling and releasing from the mould are long; under industrial production conditions, the cycle times are about 20 to 50 minutes. Because of these long cycle times, a large number of individual moulds, associated with high investment costs, is needed. In addition, the energy used for heating and cooling the moulds is high.

Since the teeth have flashes after removal from the mould, expensive subsequent working steps, such as, for example, tumbling and polishing, are necessary. Overall, the chemoplastic process is far less economical than the thermoplastic process.

The known chemoplastic process is severely limited in respect of the possibility of varying the starting materials employed. Thus, only simple alkylene dimethacrylates which partly dissolve the polymer powder at a low temperature can be used as the crosslinking agent.

The object of the invention was to provide a process for the production of crosslinked dental mouldings which does not have the disadvantages described above. This object is achieved by a specific process which is based on thermoplastic shaping and subsequent crosslinking by photopolymerisation.

The invention thus relates to crosslinked dental mouldings and to a process for the production of these dental mouldings, which is characterised in that a mixture containing

| | |
|---|---|
| a) 40 to 90% by wt. | of polymer component having a solubility parameter of 8 to 12.5 (cal/cm$^3$)$^{\frac{1}{2}}$ of 40 to 100% by weight of non-crosslinked and 0 to 60% by weight of crosslinked polymer |
| b) 10 to 60% by wt. | of monomer component containing 0 to 90% by weight of monofunctional (meth)acrylic acid ester and 10 to 100% by weight of polyfunctional (meth)acrylic acid ester | and c) 0.1 to 5% by wt. of photoactivator is processed to shaped articles by a thermoplastic process and then crosslinked by photopolymerisation.

The crosslinked dental mouldings according to the invention are, for example, false teeth, crowns, bridges, veneer shells, inlays and onlays. The new process can be used particularly advantageously for the production of false teeth.

The polymer component (a) employed according to the invention has a solubility parameter of 8 to 12.5, preferably 8.5 to 12 $(cal/cm^3)^{\frac{1}{2}}$. The solubility parameters of important known polymers and calculation methods for new polymer compositions are described in the literature, for example in the Polymer Handbook 3rd Edition, Brandrup und Immergut, John Weley and Sons, New York, 1989.

Examples of suitable polymers are polyesters, polycarbonates, polyester-polycarbonate copolymers and vinyl polymers, such as styrene-acrylate copolymers, styrene-acrylonitrile-acrylate terpolymers and polyvinyl esters. Preferred polymers are homo- and copolymers of (meth)-acrylic acid esters. Polymethyl methacrylate and copolymers of methyl methacrylate with $C_1$-$C_8$-alkyl (meth)acrylates as the comonomer are particularly preferred. Particularly suitable comonomers are ethyl acrylate, n-butyl acrylate, iso-butyl acrylate, n-butyl methacrylate, isobutyl methacrylate, ethylhexyl acrylate, n-octyl acrylate and ethylhexyl methacrylate.

The monomer component (b) contains 0 to 90 % by weight, preferably 0 to 80 % by weight, particularly preferably 0 to 60 % by weight, of monofunctional (meth)acrylic acid esters and 10 to 100 % by weight, preferably 20 to 100 % by weight, particularly preferably 40 to 100 % by weight, of polyfunctional (meth)acrylic acid esters.

Suitable monofunctional methacrylic acid esters are, for example, methyl methacrylate, ethyl acrylate, n-propyl methacrylate, iso-propyl methacrylate, n-butyl acrylate, n-butyl methacrylate, iso-butyl methacrylate, n-hexyl methacrylate, ethylhexyl acrylate, ethylhexyl methacrylate, n-octyl methacrylate, cyclohexyl acrylate, cyclohexyl methacrylate, phenylethyl acrylate, phenylethyl methacrylate, 2-methoxyethyl methacrylate, triethylene glycol monomethacrylate, 3-methoxybutylmethacrylate, butoxyethyl acrylate, furfuryl methacrylate and tetrahydrofurfuryl acrylate.

The term polyfunctional (meth)acrylic acid esters means esters of acrylic acid and methacrylic acid having two or more polymerisable double bonds. Esters of di- to octavalent alcohols having 2 to 30 carbon atoms may be mentioned as preferred. Epoxide (meth)acrylates and urethane (meth)acrylates are particularly preferred.

Examples which may be mentioned are (meth)acrylic acid esters of the formula

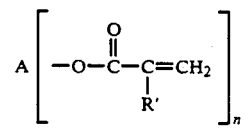

in which

A denotes a straight-chain, branched, cyclic, aliphatic, aromatic or mixed aliphatic-aromatic radical having 2 to 30 C atoms, which can be interrupted —O—or NH bridges and can be substituted by hydroxyl, oxy, carboxyl, amino or halogen, R' denotes H or methyl and n represents an integer from 2 to 8, preferably 2 to 4.

The compounds of the following formulae may be mentioned as preferred:

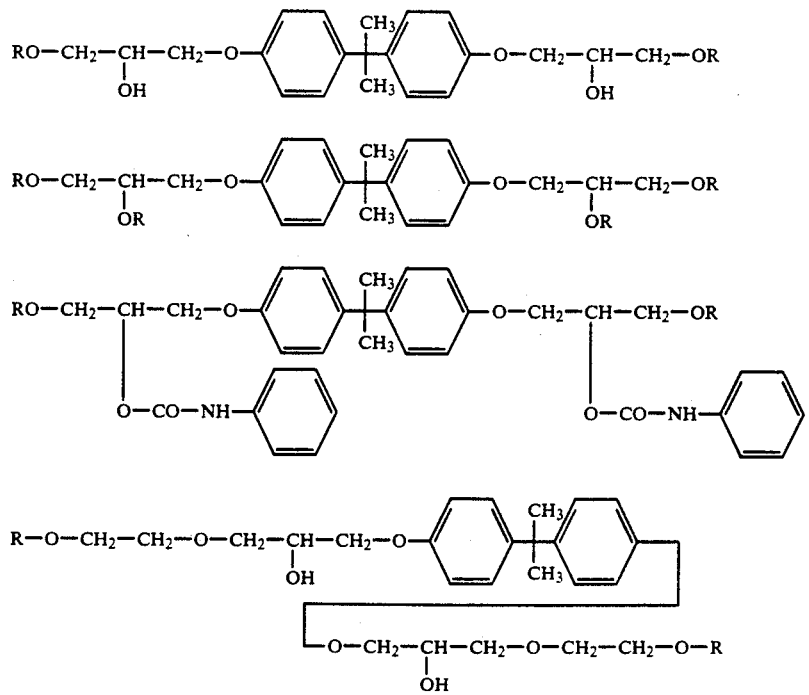

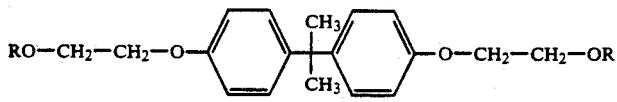
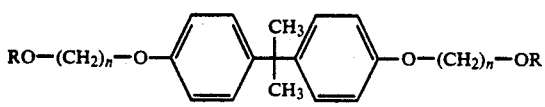
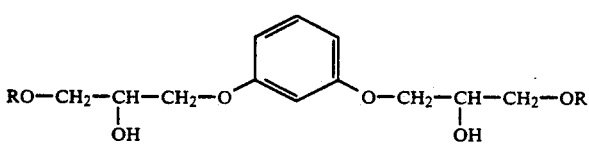
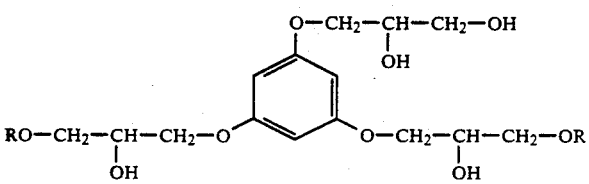
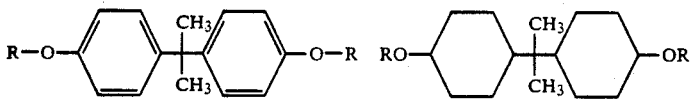
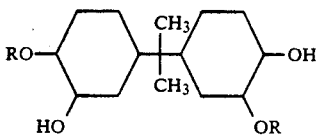
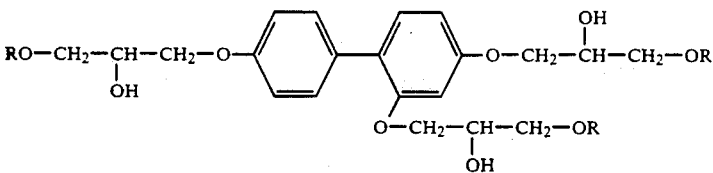
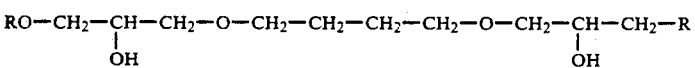
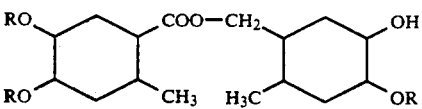
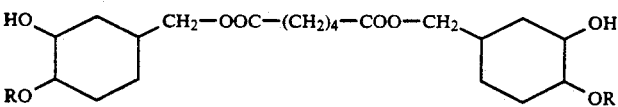
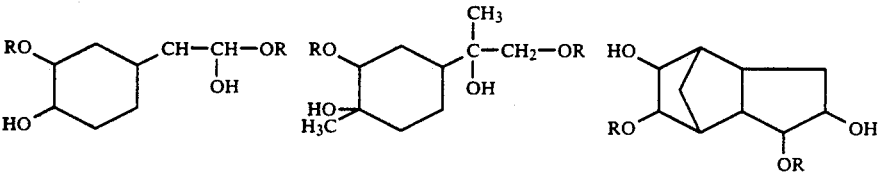
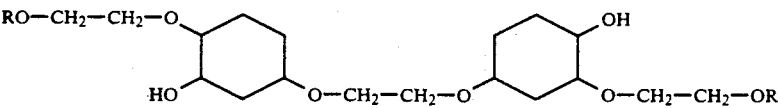

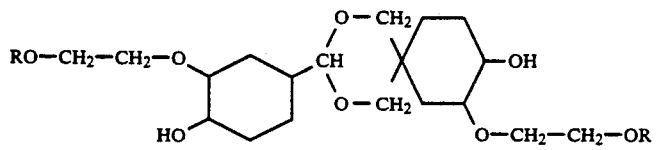
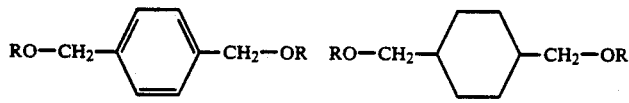
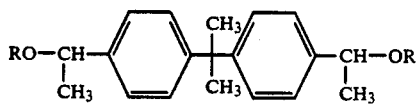
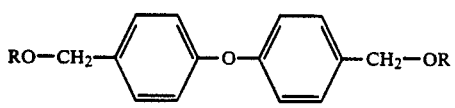
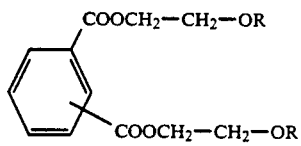
in the ortho, meta or para form
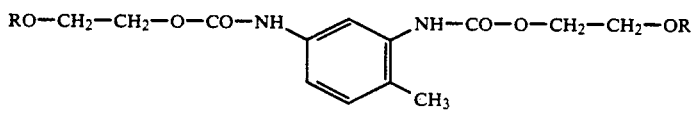
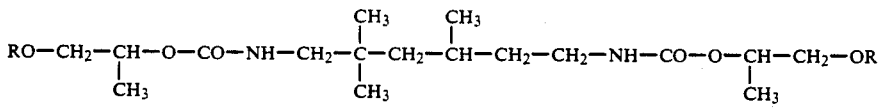
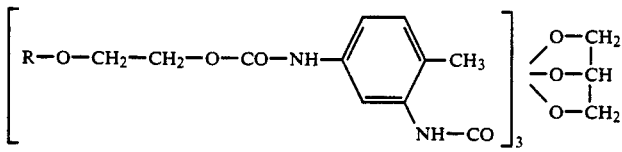
wherein R represents
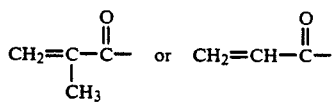
Derivatives of tricyclodecane (EP-A 0,023,686) and reaction products of polyols, diisocyanates and hydroxyalkyl methacrylates (DE-A 3,703,120, DE-A 3,703,080 and DE-A 3,703,130) may also be mentioned. The following monomers may be mentioned as examples:
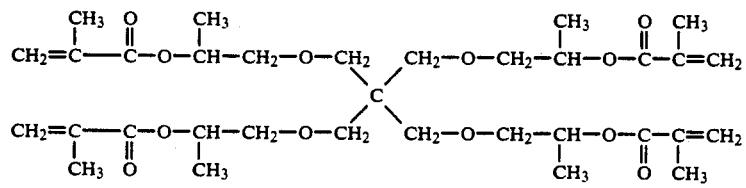
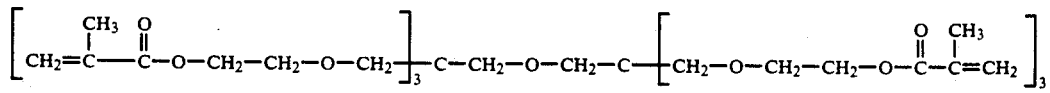

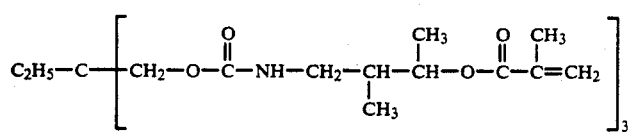
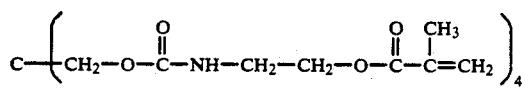
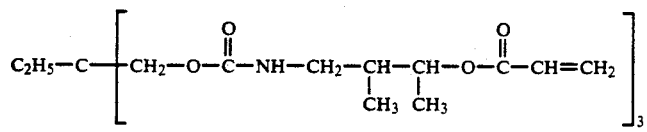
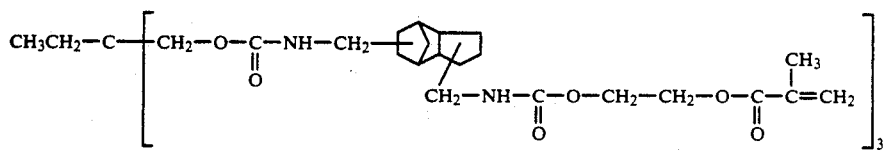
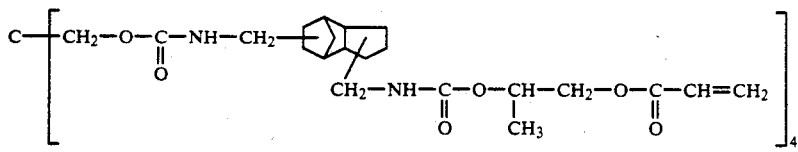
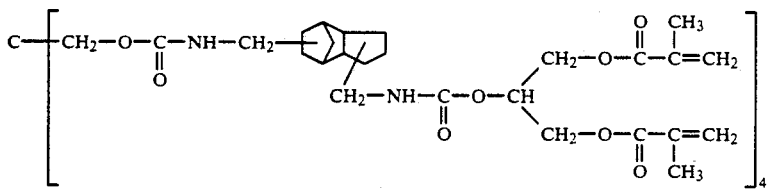
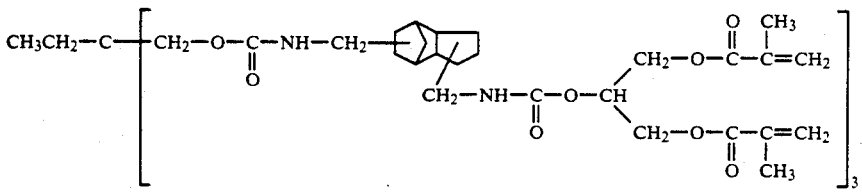
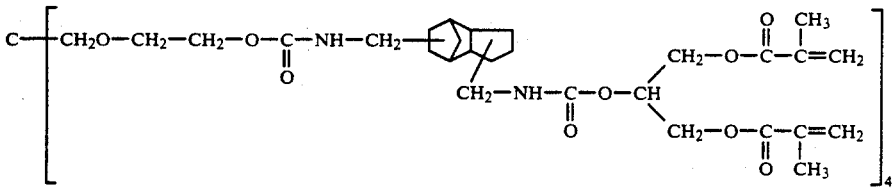
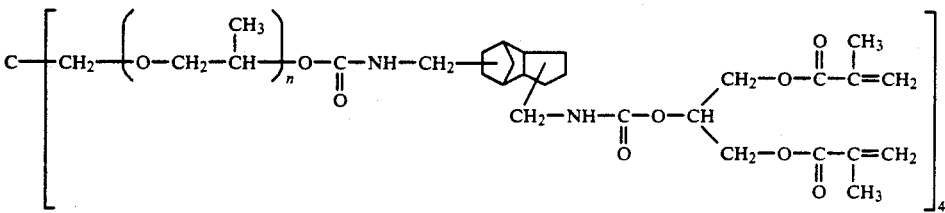
'n = 1.225 (statistical mean for 4 chains)

-continued
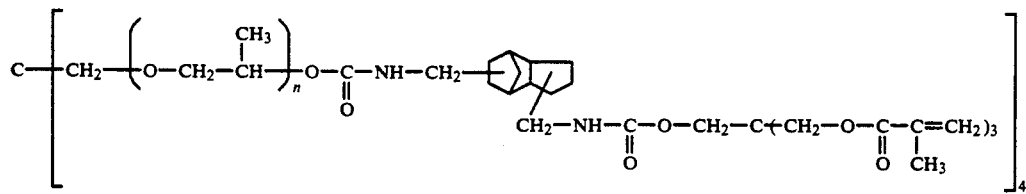
n = 1.225 (statistical mean for 4 chains)
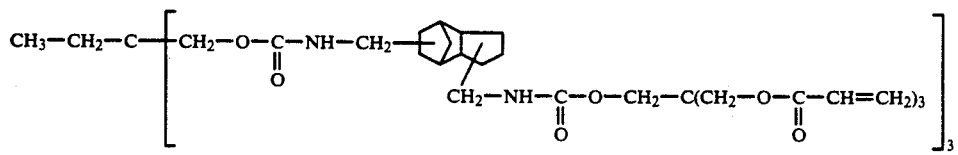
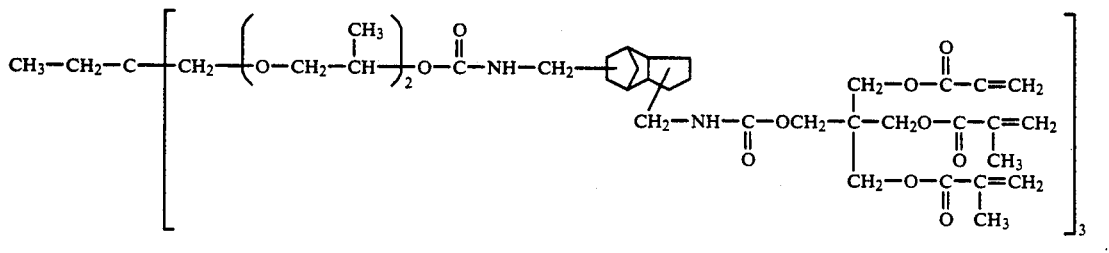
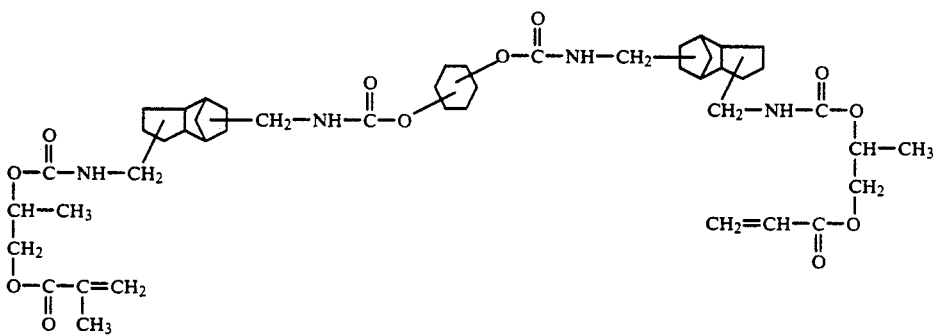
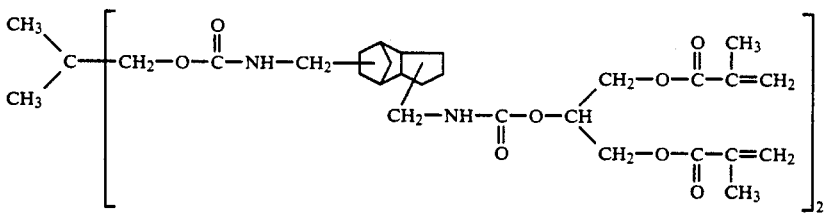
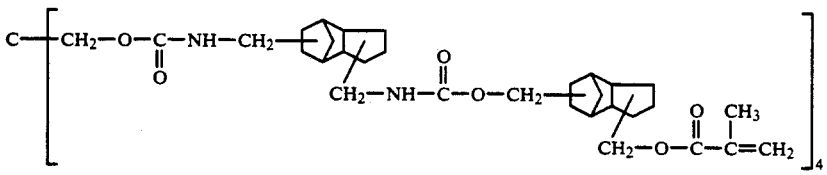
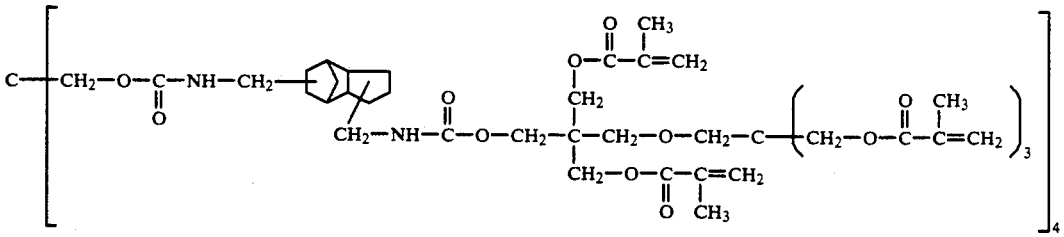

-continued
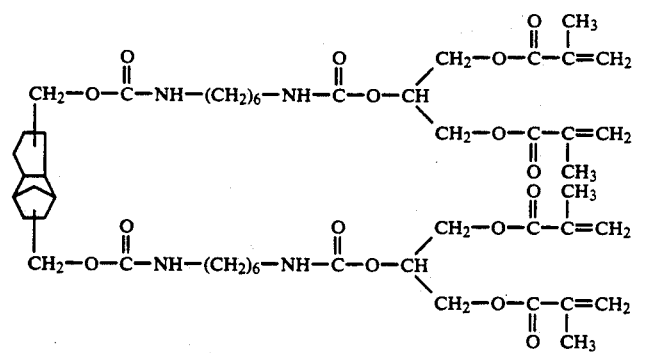
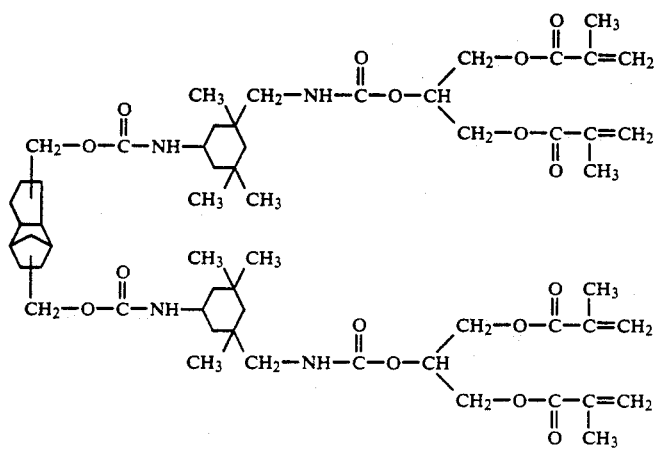
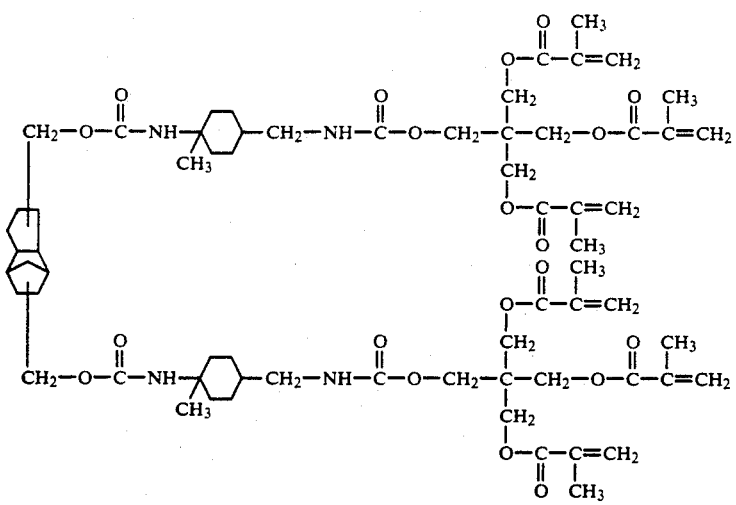
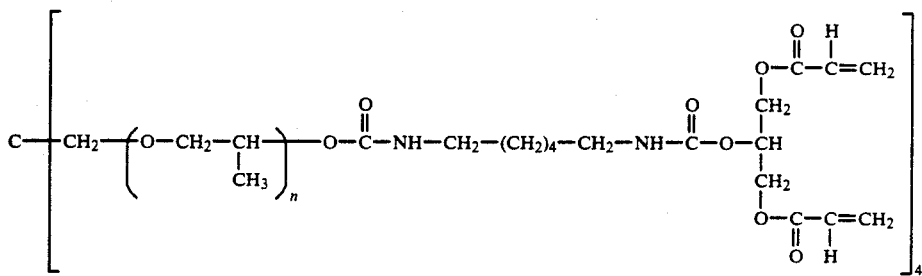
n = 1.225 (statistical mean for 4 chains)

-continued

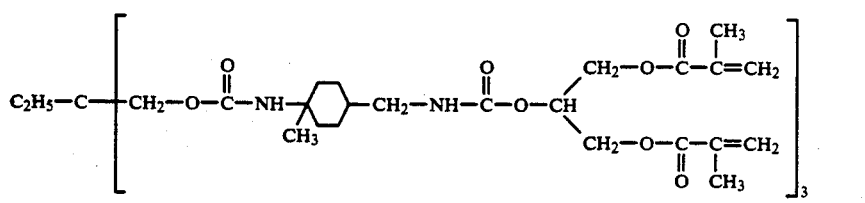

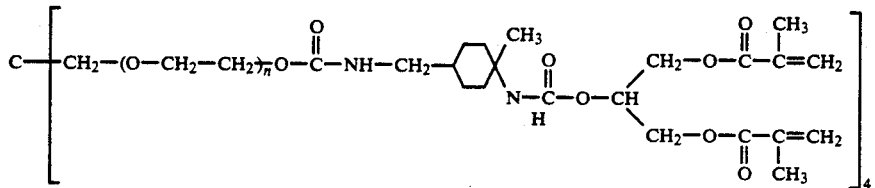

n = 1.225 (statistical mean for 4 chains)

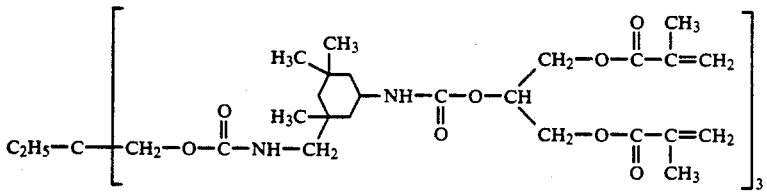

A particularly preferred (meth)acrylic acid ester is so-called bis-GMA of the formula

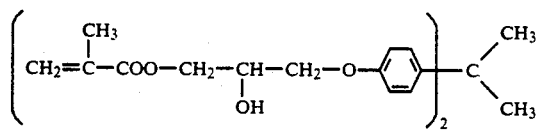

It is of course possible to employ mixtures of different monofunctional and/or polyfunctional (meth)-acrylic acid esters.

the mixtures according to the invention in general contain 0.1 to 5%, preferably 0.25 to 1%, of a photoactivator. The photoactivator consists of a photopolymerisation initiator and if appropriate additionally a coactivator.

Photopolymerisation initiators in the context of the present invention are agents which form free radicals which trigger off free radical polymerisation under the action of light, for example UV light, visible light or laser light.

Photopolymerisation initiators are known per se (see, for example, Houben Weyl, Methoden der organischen Chemie (Methods of organic chemistry), Volume E 20, Page 80 et seq., Georg Thieme Verlag Stuttgart, 1987). They are preferably mono- or dicarbonyl compounds, such as benzoin and derivatives thereof, in particular benzoin methyl ether, benzil and benzil derivatives, for example 4,4-oxydibenzil, and other dicarbonyl compounds, such as diacetyl, 2,3-pentanedione and α-diketo derivatives of norbornane and substituted norbornanes, such as, for example, camphorquinone, metal carbonyls, such as manganese pentacarbonyl, or quinones, such as 9,10-phenanthrenequinone and naphthoquinone.

In general, in addition to the actual photopolymerisation initiator, the mixture also contains a coactivator which accelerates the photopolymerisation. Known coactivators are, for example, amines, such as p-toluidine, N,N-dimethyl-p-toluidine, trialkylamines, such as trihexylamine, polyamines, such as N,N,N',N'-tetraalkylalkylenediamines, barbituric acid and dialkylbarbituric acids. Dimethylaminobenzenesulphonamides according to DOS (German Offenlegungsschrift) 3,135,113 are also particularly suitable.

The ratio of photopolymerisation initiator to coactivator is in general 1:1 to 1:3, and in many cases a ratio of 1:2 can be used.

In addition to components a), b) and c), the mixture can of course contain as further components all the additives which are usually used for the production of dental mouldings.

It is thus possible to add UV stabilisers to avoid subsequent darkening during ageing. A particularly suitable stabiliser is 2-hydroxy-4-methoxybenzophenone. 2-(2'-Hydroxy-5-methylphenyl)-benzotriazole may be mentioned as a further example.

Pigments and dyestuffs which are known per se can be used to establish a colour which is as natural-looking as possible.

The mixture of components a), b) and c) can be prepared by compounding in high-performance mixing units, such as kneaders or twin-screw extruders. The mixing temperature here is in general in the range from 110° to 180° C., preferably 120° to 160° C. It has been found that no undesirable premature crosslinking occurs under these conditions.

Mixing can also be facilitated by addition of solvents, such as acetone, methyl ethyl ketone, tetrahydrofuran, dioxane, ethyl acetate, methylene chloride and chloroform. A preferred solvent is methyl ethyl ketone. After the mixing operation, the solvent can be removed, for example, with the aid of a devolatilisation extruder. The extrusion is advantageously followed by a granulating step.

Shaping is carried out by thermoplastic processing, preferably by injection moulding. The optimum temperatures of the injection moulding process depend on the nature and composition of components a) and b) and can be determined by simple preliminary experiments. For example, the following temperatures have been determined as being particularly favourable for a mixture of polymethyl methacrylate and bis-GMA:

| Melt temperature | 130–140° C. |
|---|---|
| Die temperature | 160–170° C. |
| Mould temperature | 30–40° C. |

In many cases, the optimum melt temperature is in the range from 110° to 180° C.

Commercially available injection moulding machines with, for example, tooth moulds as the mould are suitable for the processing. Several layers can be injected in succession by using blenders and by an appropriate design of the mould. The bonding of the layers to one another is good. The cycle time for an injection operation is about 10 to 60 s.

After release from the mould, the dental mouldings obtained have adequate strength and dimensional stability, so that they are not deformed or damaged during further working The mouldings are crosslinked under the action of light. Light of various wavelengths, for example visible light or UV light, is suitable in principle. The emission spectrum of the light source and the spectral sensitivity of the photoinitiator used must of course be matched to one another.

The radiation sources used are powerful lamps or, particularly advantageously, so-called light ovens which allow a good control of the temperature and the use of an inert gas.

Photo-DSC (Differential Scanning Calorimetry) is particularly suitable for characterising the photopolymerisation. Using this method, the heats of polymerisation can be determined as a measure of the polymerisation conversions for a given recipe as a function of the experimental conditions. The polymerisation conversion in general increases as the radiation intensity, radiation time and temperature increase.

It is particularly advantageous to increase the temperature during the polymerisation, for example from 50° C. to 90° C. Both a good dimensional accuracy and a high polymerisation conversion are achieved in this manner.

The irradiation time needed depends on the intensity of the radiation source and the layer thickness of the dental moulding. Customary irradiation times are in the region of a few minutes, for example 1 to 15 minutes.

The irradiation can also be followed by after-treatment by heating (annealing). This after-treatment by heating is advantageously carried out at a temperature above the glass transition temperature of polymer component (a). A temperature of 120° to 150° C. and a heat treatment time of 3 to 12 hours is particularly suitable for shaped articles containing polymethyl methacrylate. Any stresses present are removed and the residual monomer content, which is low according to the invention, is reduced still further by this heat treatment.

The shaped articles produced by the process according to the invention have a particularly high mechanical strength and resistance to solvents. The significantly improved wear resistance compared with materials of the prior art is to be emphasised in particular.

Example 1

Preparation of granules

The components listed below are mixed homogeneously and processed to granules having a diameter of about 5 mm in a compounding screw extruder with a downstream granulator:

| 2,585.60 g | of polymethyl methacrylate bead polymer (molecular weight Mw 450,000) |
|---|---|
| 976.00 g | of bis-GMA 2,2-bis-[p-(2'-hydroxy-3'-methacryloxy-propyl)-phenyl]-propane |
| 416.00 g | of triethylene glycol dimethacrylate |
| 5.60 g | of camphorquinone |
| 14.00 g | of p-dimethylamino-benzenesulphonic acid N,N-diallylamide |
| 2.80 g | of 2,6-di-tert.-butylkresol. |

The melt temperature in the extruder was 140° C. and the viscosity of the melt at this temperature was 2,000 Pa.s, measured at a shear rate of 100/s. The granules obtained were protected from the action of light during preparation, storage and further processing.

Example 2

Injection moulding

The granules from Example 1 were injection-moulded to teeth in metal moulds using an injection moulding machine of the Engel 433 type. The following experimental conditions were observed during this process:

| Melt temperature: | 140 to 150° C. |
|---|---|
| Die temperature: | 160° C. |
| Mould temperature: | 35 to 40° C. |
| Locking force: | 600 kN |
| Screw speed: | 200/minute |
| Injection time: | 4 seconds |
| After-pressure time: | 12 seconds |
| Cooling time: | 20 seconds |
| Pause time: | 3 seconds |
| Cycle time: | about 40 seconds |

Example 3

Investigation of the photopolymerisation

The photopolymerisation of the mixture from Example 1 was investigated in a photo-DSC, by a procedure in which cylindrical test specimens (diameter: 5 mm, height: 1 mm) produced at 140° C. were irradiated with a 75 W halogen lamp with a heat protection filter in the DSC apparatus. Both the reaction enthalpy (delta H, as a measure of the polymerisation conversion) and the time taken to reach the maximum rate of reaction (t-max) were measured at 50, 70° and 90° C.:

| Measurement temperature | Delta H | t-Max. |
|---|---|---|
| 50° C. | 21 J/g | 5.6 min. |
| 70° C. | 36 J/g | 2.9 min. |
| 90° C. | 51 J/g | 2.0 min. |

The reaction enthalpy of 51 J/g corresponds to virtually complete conversion, which was confirmed by infrared spectroscopic determination of the double-bond content.

Example 4

Photopolymerisation

Injection-moulded teeth from Example 2 were irradiated at 50° C. for 8 minutes and at 90° C. for a further 5 minutes and then heat-treated at 130° C. for 3 hours in a light oven fitted with halogen lamps (output 75 W)

while flushing with nitrogen. The resulting teeth made of plastic had good hardness, high wear resistance and good resistance to solvents.

We claim:

1. A process for the preparation of a molded dental article, said process comprising the following steps:
    (a) shaping a curable solid composition into a dental mold using a thermoplastic shaping process to yield a shaped curable solid composition; removing the curable solid shaped composition from the mold; and
    (b) crosslinking the shaped curable solid composition by photopolymerisation to yield said molded dental article;
wherein said curable solid composition comprises the following ingredients:
    (i) 40 to 90% by weight of a polymer component having a solubility parameter of 8–12.5 $(cal/cm^3)^{\frac{1}{2}}$ of 40–100% by weight of non-crosslinked and 0–60% by weight of crosslinked polymer;
    (ii) 10 to 60% by weight of monomer component containing 0 to 90% by weight of monofunctional (meth)acrylic acid ester and 10 to 100% by weight of polyfunctional (meth)acrylic acid ester; and
    (iii) 0.1 to 5% by weight of photoactivator.

2. The method according to claim 1, wherein the curable composition comprises:
    (a) 40 to 90% by weight of polymer component having a solubility parameter of 8–12.5 $(cal/cm^3)^{\frac{1}{2}}$ of 40–100% by weight of non-crosslinked polymer;
    (b) 10 to 60% by weight of polyfunctional (meth)acrylic acid ester;
    and
    (c) 0.1 to 5% by weight of photoactivator.

3. The method according to claim 1, wherein the thermoplastic shaping process is injection molding.

* * * * *

UNITED STATES PATENT AND TRADEMARK OFFICE
CERTIFICATE OF CORRECTION

PATENT NO. : 5,270,350
DATED : December 14, 1993
INVENTOR(S) : Michael Müller et al It is certified that error appears in the above-indentified patent and that said Letters Patent is hereby corrected as shown below:

Col. 20, line 9      After " curable" insert -- solid --

Signed and Sealed this

Twenty-seventh Day of June, 1995

Attest:

BRUCE LEHMAN

Attesting Officer      Commissioner of Patents and Trademarks